United States Patent [19]

Riepl et al.

[11] Patent Number: 5,268,495
[45] Date of Patent: Dec. 7, 1993

[54] METALLOCENES HAVING BICYCLIC CYCLOPENTADIENE DERIVATIVES AS LIGANDS, PROCESSES FOR THEIR PREPARATION AND THEIR USE AS CATALYSTS

[75] Inventors: Herbert Riepl, Dachau; Wolfgang A. Herrmann, Freising; Jürgen Rohrmann, Liederbach, all of Fed. Rep. of Germany

[73] Assignee: Hoechst Aktiengesellschaft, Frankfurt, Fed. Rep. of Germany

[21] Appl. No.: 803,598

[22] Filed: Dec. 9, 1991

[30] Foreign Application Priority Data

Dec. 11, 1990 [DE] Fed. Rep. of Germany ....... 4039451

[51] Int. Cl.$^5$ ............................ C07F 7/28; C07F 17/00
[52] U.S. Cl. ..................................... 556/11; 556/12; 556/43; 556/53; 556/87
[58] Field of Search .................. 556/11, 12, 43, 53, 556/87

[56] References Cited

U.S. PATENT DOCUMENTS 4,769,510 9/1988 Kaminsky et al. ............... 385/512

FOREIGN PATENT DOCUMENTS 0316155 5/1989 European Pat. Off. .
0344887 6/1989 European Pat. Off. .
0185918 9/1989 European Pat. Off. .
0420436 3/1991 European Pat. Off. .

OTHER PUBLICATIONS

Journal of Organic Chemistry, Bd. 39, Nr. 18, (1974), pp. 2783-2787.
Experientia 11, (1955) p. 115.
J. Chem. Soc. Chem. Commun. (1978), pp. 601-602.
Tetrahedron Lett. (1977), pp. 159-162.
C. R. Acad. Sci. Paris 267 (1968), pp. 467-470.
Mise, T. et al, *Chemistry Letters,* Japan, The Chemical Society of Japan, (1989), pp. 1853-1856.

*Primary Examiner*—Jose' G. Dees
*Assistant Examiner*—Porfirio Nazario
*Attorney, Agent, or Firm*—Connolly and Hutz

[57] ABSTRACT

The invention relates to a process for the preparation of a compound of the formula XI

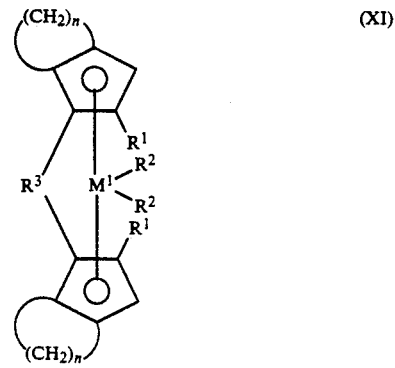

wherein preferably $M^1$ is zirconium, the radicals $R^1$ are alkyl, the radicals $R^2$ are halogen or alkyl, $R^3$ is dimethylsilyl or ethylene and n is 2-18, wherein a compound of the formula II

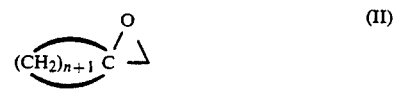

is reacted with an alkali metal or alkaline earth metal salt of a malonic ester and then with an alkyl halide, the reaction product is converted by decarboxylation into the corresponding lactone, which is further reacted by known methods to give the compound XI.

The compounds of the formula XI, some of which are novel, can advantageously be used as catalysts for olefin polymerization.

17 Claims, No Drawings

METALLOCENES HAVING BICYCLIC CYCLOPENTADIENE DERIVATIVES AS LIGANDS, PROCESSES FOR THEIR PREPARATION AND THEIR USE AS CATALYSTS

The present invention relates primarily to a process for the preparation of metallocenes which carry bicyclic derivatives of cyclopentadiene as ligands. The majority of these compounds are novel and can advantageously be used as catalysts for the preparation of polyolefins which are characterized in particular by high stereospecificity, a high melting point and good crystallinity. Such polymers are suitable, inter alia, as structural materials (large hollow articles, pipes, moldings).

Derivatives of zirconocene dichloride which are substituted in the ring and in which the two substituted cyclopentadienyl groups are bonded to one another via an ethylene or a dimethylsilylene bridge have a rigid conformation and can therefore be used as catalysts for the stereospecific polymerization of propene. The type and arrangement of the substituents influence the polymerization rate, the average molecular weight and the isotacticity (Chem. Lett. 1989, pages 1853-1856 or EP-A 0 316 155).

Among the bicyclic derivatives of cyclopentadiene, (substituted) indenyl radicals are important as ligands for metallocenes (polymerization catalysts). Thus, for example, the preparation of isotactic polypropylene with the aid of the catalyst system ethylenebis(4,5,6,7-tetrahydro-1-indenyl)zirconiumdichloride/aluminoxane has been described (EP-A 185 918).

Bridged metallocenes which carry bicyclic derivatives of cyclopentadiene as ligands, where the cyclopentadienyl moiety may additionally be substituted, are likely to have interesting properties and should be capable of considerably extending the property spectrum of the polymers which can be prepared The use of such catalysts was unsuccessful to date because there was no feasible synthesis method for such complexes which are substituted in particular in the 2-position on the cyclopentadienyl moiety.

The present invention therefore relates to a process for the preparation of a compound of the formula XI

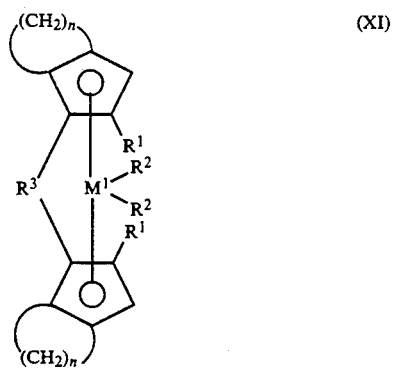

wherein $M^1$ is a metal from the group comprising titanium, zirconium, hafnium, vanadium, niobium and tantalum, the radicals $R^1$ are identical or different and are hydrogen, a $C_1$-$C_{10}$-alkyl group, a $C_6$-$C_{10}$-aryl group, a $C_7$-$C_{15}$-arylalkyl group or a $C_2$-$C_{10}$-alkenyl group, the radicals $R^2$ are identical or different and are a $C_1$-$C_{10}$-alkyl group, a $C_1$-$C_{10}$-alkoxy group, a $C_6$-$C_{10}$-aryl group, a $C_6$-$C_{10}$-aryloxy group, a $C_2$-$C_{10}$-alkenyl group, a $C_7$-$C_{40}$-arylalkyl group, a $C_7$-$C_{40}$-alkylaryl group, a $C_8$-$C_{40}$-arylalkenyl group or a halogen atom, $R^3$ is

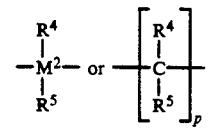

in which $M^2$ is silicon, germanium or tin, $R^4$ and $R^5$ are identical or different and are a hydrogen atom, a halogen atom, a $C_1$-$C_{10}$-alkyl group, a $C_6$-$C_{10}$-aryl group, a $C_2$-$C_{10}$-alkenyl group, a $C_7$-$C_{40}$-arylalkyl group, a $C_8$-$C_{40}$-arylalkenyl group or a $C_7$-$C_{40}$-alkylaryl group or $R^4$ and $R^5$, together with the atom which binds them, form a ring and p is 1, 2 or 3, and n is an integer from 2 to 18, wherein a compound of the formula II

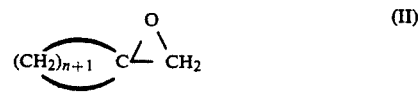

is reacted with an alkali metal or alkaline earth metal salt of a malonic ester, the intermediate formed is reacted, without isolation, with a compound $R^1$-X, in which $R^1$ has the stated meaning and X is a nucleophilic leaving group, and the reaction product is converted by decarboxylation into a lactone of the formula IV

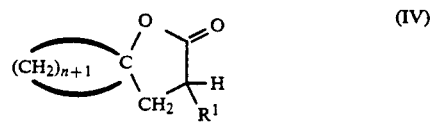

which is subjected to a rearrangement reaction to give the corresponding enone and then further reacted by known methods to give the compound of the formula XI.

In the formula XI, preferably $M^1$ is titanium, zirconium or hafnium, the radicals $R^1$ are identical and are a $C_1$-$C_4$-alkyl group, the radicals $R^2$ are identical and are halogen or a $C_1$-$C_4$-alkyl group, $M^2$ is silicon, $R^4$ and $R^5$ are identical or different and are hydrogen or a $C_1$-$C_4$-alkyl group, p is 1 or 2 and n is an integer from 4 to 7.

In particular, $M^1$ is zirconium, the radicals $R^1$ are identical and are methyl or ethyl, the radicals $R^2$ are identical and are chlorine or methyl, $M^2$ is silicon, $R^4$ and $R^5$ are hydrogen or methyl, p is 2 and n is an integer from 4 to 7.

The present invention furthermore relates to the compounds of the formula XI, including the stated preferred ranges, except for the compounds where n=4. n is thus preferably a number from 5 to 7.

The preparation of the compounds XI is illustrated, by way of example, by the following reaction schemes 1 and 2:
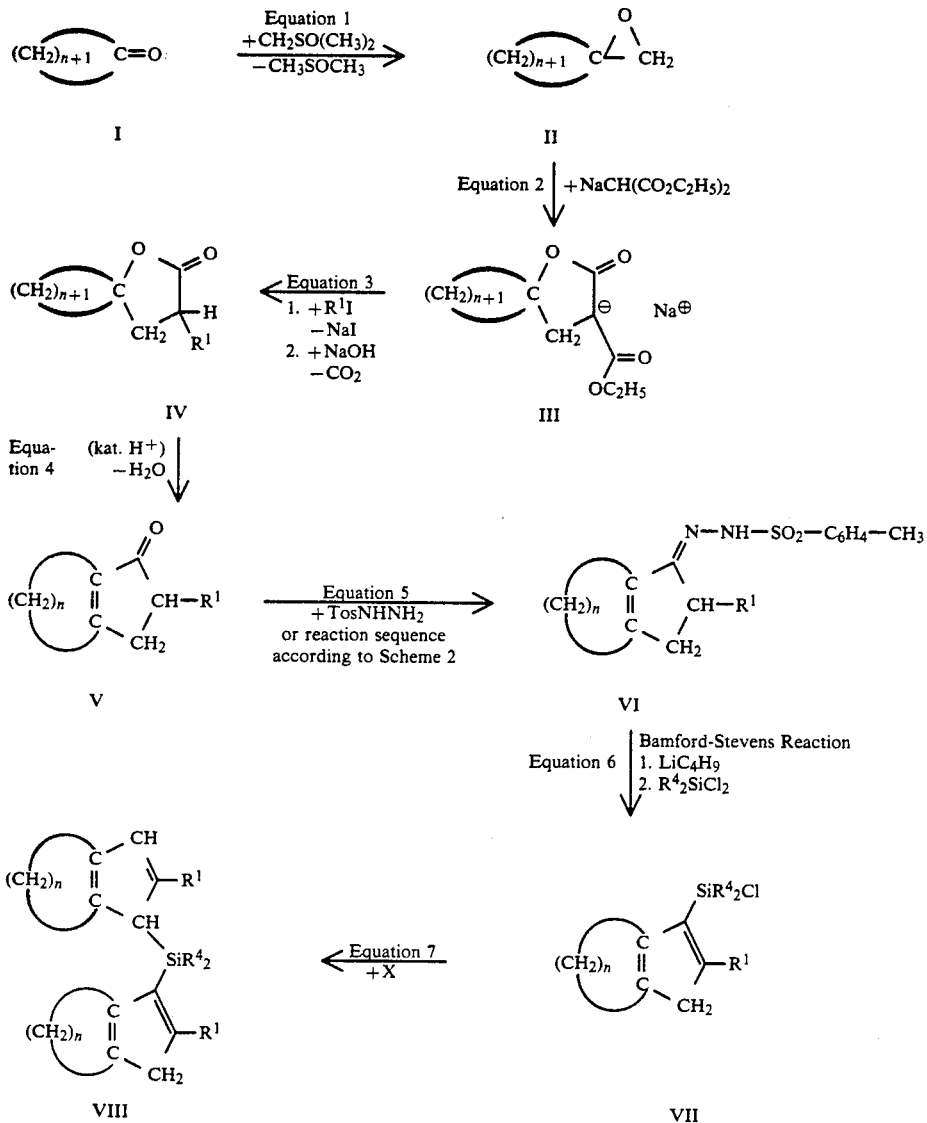
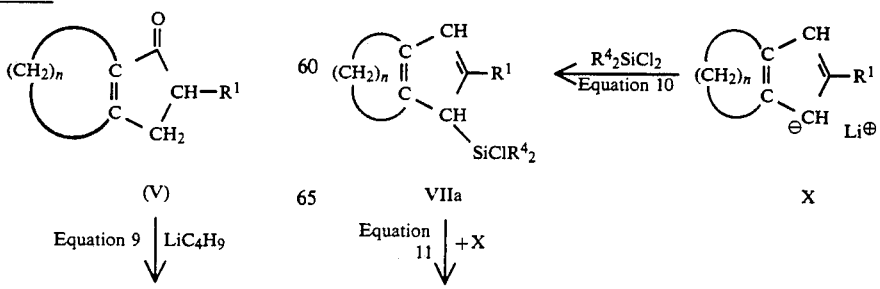

Scheme 2 -continued

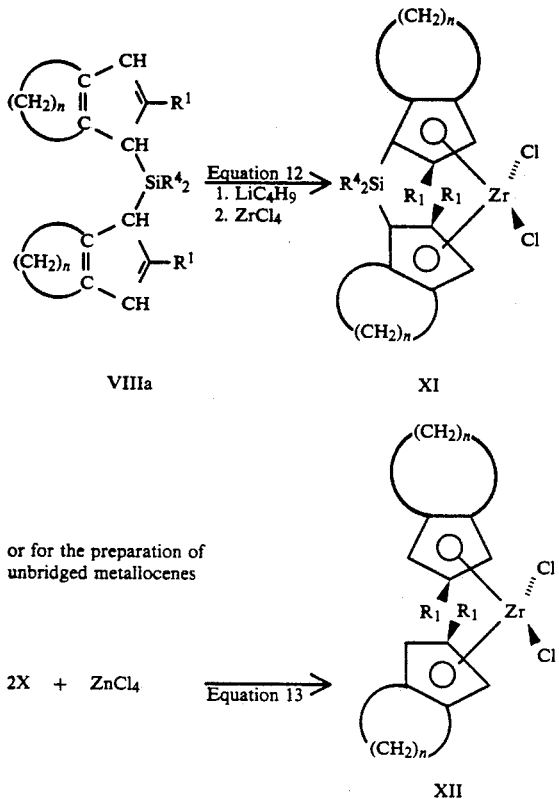

or for the preparation of unbridged metallocenes $2X + ZnCl_4 \xrightarrow{\text{Equation 13}}$ XII According to Scheme 1, the starting materials used are cyclic ketones I, such as, for example, cycloheptanone or cyclooctanone (n=5, 6). In a first step applicable to large batches, this ketone is converted, for example with trimethyloxosulfurane, into the epoxide II (Equation 1). The subsequent central step in the synthesis of the compounds XI, which also simultaneously solves the problem of introducing the substituent $R^1$ in the α-position to the bridge $R^3$ (substitution in the 2-position on the subsequent cyclopentadienyl moiety), consists in cleaving the epoxide with the anion of a malonic ester (Equation 2). This is carried out by reacting the epoxide II with an alkali metal or alkaline earth metal salt of an alkyl, aryl or alkenyl, preferably ($C_1$-$C_{10}$)-alkyl, in particular ($C_1$-$C_4$)-alkyl ester of malonic acid. The di-($C_1$-$C_4$)-alkyl malonates are particularly preferred, and among these diethyl malonate. These esters are preferably used in the form of their sodium salt.

A salt-like mass having the presumed constitution III is obtained as a first product. It is reacted, without isolation, with a compound $R^1$-X, in which X is a leaving group, such as halogen, preferably bromine or iodine, or tosyl. Working up in the alkaline medium and subsequent distillation leads to decarboxylation (Equation 3).

The lactone IV thus obtained can be subjected to a rearrangement reaction—by known methods—by stirring in acidic media (for example polyphosphoric acid/$P_2O_5$ or methanesulfonic acid/$P_2O_5$) to give an enone V, which is the starting material of the diene synthesis (Equation 4). This step could be optimized to such an extent that it gives the enone in 92% yield. The fact that the reaction (preferably alkylation) of the lactonate ion takes place virtually quantitatively according to Equation 3 is advantageous, and expensive distillative separation operations are therefore dispensed with. In view of the thermal sensitivity of the enone, this is an important detail.

V can be reduced in a classical manner by reducing agents such as sodium boranate in the presence of cerium(III) chloride or lithium aluminum hydride. However, the corresponding allyl alcohol is not isolated; instead, a mixture of the three cyclopentadienyl derivatives IX, which are positional isomers, are obtained directly (Equation 8, Scheme 2).

The reaction, known from the literature, of the diene IX with a compound $M^3$-R ($M^3$=an alkali metal, R=alkyl or hydrogen; in this case, for example, butyllithium, Equation 9) and subsequent introduction of the bridge $R^3$ (in the form of a compound X-$R^3$-X in which X=Cl, Br or tosyl; in this case, for example, $R^4_2SiCl_2$, Equation 10) leads to the compound of the formula VIIa.

If the other double bond isomer VII is desired, it can be obtained by the "Bamford-Stevens method", for example via the tosylhydrazone VI (Equations 5 and 6).

The reaction of the isomers VII/VIIa with the alkali metal salt X, preferably the lithium salt, gives the ligand system VIII/VIIIa in good yields (Equations 7 and 11). The preparation of the metal complexes XI is carried out by deprotonation of the cyclopentadiene system VIII/VIIIa with a compound of the type $M^3$-R (see above; preferably butyllithium) and reaction of the resulting dilithio salt with a compound of the formula $M^1X_4$ (X=halogen, preferably chlorine, in particular zirconium tetrachloride) in suitable solvents (for example dimethoxyethane, Equation 12). The resulting reaction product XI is a mixture of the rac and meso complexes. Unbridged metal complexes of the type XII are obtainable by reacting the lithium salts X with $M^1X_4$ (Equation 13).

With exception of the steps corresponding to Equations 2 and 3, the stated reaction sequence is known, also with regard to the solvent, temperature and reaction time parameters; cf. Experientia 11 (1955) 114–115; J. Chem. Soc. Chem. Commun. 1978, 601–602; Tetrahedron Lett. 1977, 159–162; C. R. Acad. Sci. Paris 267 (1968) 467–470 and the examples.

The chiral metallocenes are used in the form of the racemate for the preparation of highly isotactic poly-1-olefins. However, the pure R or S form may also be used. With these pure stereoisomeric forms, it is possible to prepare an optically active polymer. However, the meso form of the metallocenes should be separated off since the active center (the metal atom) for polymerization in these compounds is no longer chiral owing to mirror symmetry at the central metal and therefore cannot produce a highly isotactic polymer.

The separation of the stereoisomers is known in principle.

According to the invention, the cocatalyst used is an aluminoxane of the formula

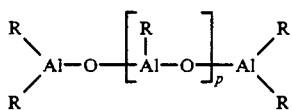

for the linear type and/or of the formula

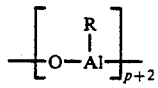

for the cyclic type, where, in the formulae, the radicals R may be identical or different and are a $C_1$-$C_6$-alkyl group, a $C_6$-$C_{18}$-aryl group or hydrogen and p is an integer from 2 to 50, preferably from 10 to 35.

Preferably, the radicals R are identical and are methyl, isobutyl, phenyl or benzyl, particularly preferably methyl.

If the radicals R are different, they are preferably methyl and hydrogen or alternatively methyl and isobutyl, hydrogen or isobutyl preferably being present in an amount of 0.01–40% (number of radicals R).

The aluminoxane can be prepared in various ways by known processes. One of the methods comprises, for example, reacting an aluminum-hydrocarbon compound and/or the hydridoaluminum-hydrocarbon compound with water (gaseous, solid, liquid or bound—for example as water of crystallization) in an inert solvent (such as, for example, toluene). For the preparation of an aluminoxane having different alkyl groups R, according to the desired composition two different aluminumtrialkyls ($AlR_3 + AlR'_3$) are reacted with water (cf. S. Pasynkiewicz, Polyhedron 9 (1990) 429–430 and EP-A 302 424).

The exact structure of the aluminoxanes is not known.

Regardless of the method of preparation, the common feature of all aluminoxane solutions is a change in content of unconverted aluminum starting compound, which is present in free form or as an adduct.

It is possible to preactivate the metallocene prior to use in the polymerization reaction with an aluminoxane. This considerably increases the polymerization activity and improves the particle morphology.

The preactivation of the transition metal compound is carried out in solution. The metallocene is preferably dissolved in a solution of the aluminoxane in an inert hydrocarbon. A suitable inert hydrocarbon is an aliphatic or aromatic hydrocarbon. Toluene is preferably used.

The concentration of the aluminoxane in the solution is in the range from about 1% by weight to the saturation limit, preferably from 5 to 30% by weight, based in each case on the total solution. The metallocene can be used in the same concentration but is preferably employed in an amount of $10^{-4}$–1 mol per mole of aluminoxane. The preactivation time is 5 minutes to 60 hours, preferably 5 to 60 minutes. The temperature of $-78°$ C. to $100°$ C., preferably $0°$ to $70°$ C., is employed.

The metallocene can also be prepolymerized or can be applied to a carrier. The olefin used in the polymerization, or one of the olefins used therein, is preferably employed for the prepolymerization.

Suitable carriers are, for example, silica gels, aluminas, solid aluminoxane or other inorganic carriers. Another suitable carrier is a polyolefin powder in finely divided form.

Another possible embodiment of the process according to the invention comprises using a salt-like compound of the formula $R_xNH_{4-x}BR'_4$ or of the formula $R_3PHBR'_4$ as a cocatalyst instead of or in addition to an aluminoxane. x is 1, 2 or 3, the radicals R are identical or different and are alkyl or aryl and R' is aryl which may furthermore be fluorinated or partially fluorinated. In this case, the catalyst consists of the reaction product of a metallocene with one of the stated compounds (cf. EP-A 277 004 and the Preparation Examples E and F).

To remove catalyst poisons present in the propylene, purification with an aluminumalkyl, for example $AlMe_3$ or $AlEt_3$, is advantageous. Either this purification can be carried out in the polymerization system itself or, before addition to the polymerization system, the propylene is brought into contact with the Al compound and then separated off again.

The polymerization or copolymerization is carried out in a known manner in solution, in suspension or in the gas phase, continuously or batchwise, in one or more stages, at a temperature of $0°$ to $150°$ C., preferably $30°$ to $80°$ C. Olefins of the formula $R^1$—CH=CH—$R^b$ are polymerized or copolymerized In this formula, $R^a$ and $R^b$ are identical or different and are a hydrogen atom or an alkyl radical of from 1 to 14 carbon atoms.

However, $R^1$ and $R^b$, together with the carbon atoms binding them, may furthermore form a ring. Examples of such olefins are ethylene, propylene, 1-butene, 1-hexene, 4-methyl-1-pentene, 1-octene, norbornene and norbornadiene. In particular, propylene and ethylene are polymerized.

If necessary, hydrogen is added as a molecular weight regulator. The total pressure in the polymerization system is 0.5 to 100 bar. Polymerization in the pressure range of 5 to 64 bar, which is of particular interest in industry, is preferred.

The metallocene is used in a concentration, based on the transition metal, of $10^{-3}$ to $10^{-8}$, preferably $10^{-4}$ to $10^{-7}$, mol of transition metal per $dm^3$ of solvent or per $dm^3$ of reactor volume. The aluminoxane is used in a concentration of $10^{-5}$ to $10^{-1}$ mol, preferably $10^{-4}$ to $10^{-2}$ mol, per $dm^3$ of solvent or per $dm^3$ of reactor volume. In principle, however, higher concentrations are also possible.

If the polymerization is carried out as a suspension or solution polymerization, an inert solvent conventionally used for the Ziegler low pressure process is employed. For example, an aliphatic or cycloaliphatic hydrocarbon is employed; butane, pentane, hexane, heptane, isooctane, cyclohexane and methylcyclohexane may be mentioned as examples of these.

A gasoline or hydrogenated diesel oil fraction may also be used. Toluene is also suitable. Polymerization is preferably carried out in the liquid monomer.

If inert solvents are used, the monomers are metered in as a gas or liquid.

The polymerization can be carried out for any time since the catalyst system to be used according to the invention shows only a slight time-dependent decrease in the polymerization activity.

The process according to the invention is distinguished by the fact that, in the temperature range between $30°$ and $80°$ C. which is of interest in industry, the metallocenes according to the invention produce polymers having a high molecular weight, high stereospecificity, a narrow molecular weight dispersity and in particular a high melting point, which is equivalent to high crystallinity and a high degree of hardness.

The Examples below are intended to illustrate the invention in detail.

The reaction sequence starting from cycloheptanone (n=5) and cyclooctanone (n=6) where $R^1$=$CH_3$ and $R^4=R^5=CH_3$ is described by way of example for all ketones I $(CH_2)_{n+1}CO$.

Unless stated otherwise, the reaction was carried out under a nitrogen atmosphere (inert gas).

1. Preparation of the Lactones IV.

16.5 g (0.71 mol) of sodium are dissolved in 550 g of absolute ethanol. 113.6 g (0.71 mol) of diethyl malonate are added dropwise to the solution which is warm to the touch. After some time, a spongy precipitate forms which consists of the sodium salt of the malonic ester. 0.70 mol of the epoxide II is then added dropwise at room temperature. After the addition is complete, the mixture is heated under reflux for 6 h. After the first two hours, the mass begins to become solid, so that mixing must be carried out with a stirrer. Thereafter, stirring is continued for a further 2 hours at 50° C., after which 85 g (0.75 mol) of methyl iodide are added dropwise at room temperature. The mixture is stirred overnight and boiled for a further 2 h on the next day. The reflux condenser is replaced with a distillation bridge, and the major part of the ethanol is distilled off. Owing to the hard consistency of the mass, distillation is supported toward the end by applying a slight vacuum, since stronger heating does not achieve the aim. The mass of sodium iodide and the ester is boiled with 280 ml of 25% strength sodium hydroxide solution until a heavy oil begins to separate out. With continuous monitoring by gas chromatography the reaction mixture is left at 70°-80° C. for a further 1 h during which solid residues also go into solution. The oil is separated off in a separating funnel and finally distilled in vacuo.

Lactone IV (n=5): $C_{11}H_{18}O_2$; C: calculated 72.5 found 72.9 H: calculated 9.8 found 9.9 b.p. 112° C. (2 mmHg), 90% of theory $^1$H-NMR (100 MHz, CDCl$_3$, 25° C.): 1.08, 1.09, D (J=6.9 Hz) 3 H; 1.43, 1.39, "D", 12H; 2.58, 2.47, 2.3, 2.25, 2.08, 1.87, "M", 4H $^{13}$C-NMR (100 MHz, CDCl$_3$, 25° C., (DEPT: —CH$_3$, —CH:+, —CH$_2$—): 178.8(O) C=O, 87.02(O) quart. C, 39.51(+)CH, 15.09(+)CH:, 46.1, 42.45, 39.95, 37.58, 28.66, 21.8, 21.42(—)CH$_2$ IR spectrometry: 2292 cm$^{-1}$ s, 2863 m, 1768 vs, 1458 m, 1378 m, 1312 w, 1284 w, 1237 m, 1175 m, 1152 m, 1030 m, 1006 m, 987 m, 936 m-s Lactone IV (n=6):

b.p. 166° C. (10 mm), 82% of theory $^1$H-NMR 1 07, 1.09, D (J=7.2 Hz) 3H; 1.39 "S" 14H; 2.61, 2.51, 2.45, 2.38, 2.3, 2.19, 2.09, "M" 4H $^{13}$C-NMR: 178.0(O) C=O, 87.8(O) quart. C, 16.3(+)CH$_3$, 46.5(+)CH 2. Subjecting the Lactone IV to a Rearrangement Reaction to Give Enones V:

150 ml of technical-grade methanesulfonic acid (99%) are thoroughly stirred with 18 g (0.48 mol) of phosphorus pentoxide for 15 minutes. During this procedure, the phosphorus pentoxide is added in small portions. 0.27 mol of lactone IV is then added dropwise. The reaction starts with spontaneous heating and maintains a temperature of 70° C. for about two hours. To complete the reaction, the mixture is allowed to stand for a further two hours in an oil bath at 60° C. The melt is now deep red and fluoresces slightly in incident sunlight. For working up, it is poured into 17% strength sodium carbonate solution (obtained from a total of 600 g of Na$_2$CO$_3$) with ice. The pale yellow emulsion is extracted three times with ether and the combined organic phases are dried with sodium sulfate and evaporated down in a rotary evaporator. The remaining oil is distilled in vacuo at as low a temperature as possible and over a short bridge.

Enone V (n=5): b.p.: 105° C. (1 mm), 93% of theory $^1$H-NMR (100 MHz, CDCl$_3$) 0.77, 0.87, D (J=7.25 Hz) 3H; 1.3, 2.1 "M" 13H;

$^{13}$C-NMR (100 MHz, CDCl$_3$) 210(o) C=O, 173 (o) C=C, 161.2 (o) C=C, 15.2(+)CH$_3$, 34.2(+)CH, 39.9, 39.5, 37.8, 28.6, 28.4(—)CH$_2$

Enone V (n=6): b.p.: Only with decomposition, 89% of theory $^1$H-NMR (400 MHz, CDCl$_3$) 1.03, 0.96, D (J=7.1 Hz) 3H; 1.31, 1.63, "D" 12H; 2.37, 2.31, 2.2, 2.09, "M" 3H;

$^{13}$C-NMR (100 MHz, CDCl$_3$): 211(o) C=O, 173.1(o) C=C, 138.8(o) C=C, 16.5 (+) CH$_3$, 39.5 (+) CH, 29.8, 28.25, 25.6, 25.4, 22.02, 22.0, 19.8, (—)CH$_2$.

The tosylhydrazones VI of the two compounds were obtained by conventional methods, by refluxing for one hour with tosylhydrazine in ethanol, with subsequent recrystallization.

$^{13}$C-NMR: 198, C=N; 170.4, C=C, 135.24, C=C; 155.5, 143.4, 129.1, 127.9, Ph; 42.1, CH; 17.62, CH—CH$_3$; 21.85, Ph-CH$_3$; 32.1, 23.38, 27.7, 26.08, 25.79, 21.4, CH$_2$.

3. Preparation of the chlorodimethylsilyl-2-methylbicyclodienes VII 10 mmol of the recrystallized tosylhydrazone VI of one of the two enones are dissolved in 40 ml of anhydrous dimethoxyethane (DME) and the solution is cooled to —50° C. 15 ml (1.6 m, 24 mmol) of butyllithium also at this temperature are added dropwise by means of a capillary (17% excess). After about half the amount, there is a virtually spontaneous color change to deep red, whereas beforehand each drop of BuLi dissolved only with a few reddish streaks, which lost their color again. Stirring is then carried out for 45 minutes at this temperature. A pressure relief valve is then mounted on the dangling tube and the apparatus is placed in a cooling bath at —10° to 5° C. Gas evolution begins shortly thereafter, and decolorization to give a yellowish liquid. This can be very greatly accelerated by sunlight. After the end of the gas evolution, the solvent is stripped off and the greenish precipitate is washed twice with hexane in order to remove excess BuLi. This very sensitive salt is taken up again with 15 ml of DME, and a large excess of freshly distilled dimethyldichlorosilane is added at —20° C. The mixture is allowed to warm up slowly to room temperature and the solvent is stripped off. Lithium chloride soon separates out, and this mass is extracted with methylene chloride and filtered. The filtrate is evaporated to dryness (yellow oil which soon becomes blue in the air). For further purification, this oil is distilled in a bulb tube. In this procedure, a bulb which is filled with Raschig rings and is likewise housed in the oven is connected between the receiver and the distillation bulb. Everything in this bulb is initially distilled at a low temperature, after which the temperature is increased in order to transfer the liquid to the receiver.

VIIa (n=5):

$^1$H-NMR (100 MHz, CDCl$_3$, 25° C.): 6.07, S, 1H; 3.27, "S", 2H; 2.44, 1.66, "M", 10H; 2.1, S, 3H; 0.09, S, 6H $^{13}$C-NMR (400 MHz, CDCl$_3$, 25° C.) 144.1, 139.7, 138.8, 135.6, 55.73, 32.8, 31.5, 30.15, 27.75, 27.6, 17.6, −0.2.

4. Preparation of the bicyclodienes IX 0.1 mol of the enone V is dissolved in 50 ml of methanol. 23.8 g of CeCl$_3$. 7H$_2$O (0.1 mol) are dissolved in 70 ml of methanol with vigorous stirring and gentle heating. The two solutions are combined in a large flask and placed on ice. 3.7 g (0.1 mol) of sodium boranate are now added in portions. A full 5 minutes should be allowed between the individual additions. The suspension evolves gas vigorously and exhibits very pronounced foaming. Half an hour after the last addition, the mixture is heated to 50° C. for 2 hours. Gas chromatography is used to check for the presence of enone. If this is not the case, concentrated HCl is added dropwise to destroy sodium boranate still present. A substantially acidic pH should be detected. The emulsion is then evaporated to dryness in a rotary evaporator under a slight vacuum. This mass is extracted with ether by a method in which vigorous stirring is carried out for 20 minutes in a conical flask. After the fourth extraction, the organic phase is checked to determine if any diene is still present. The combined organic phases are dried with sodium sulfate and distilled first at atmospheric pressure and, after removal of the ether, in vacuo at 10 mmHg.

IX (n=5): Diene mixture b.p.: 81° C. (2 mm)

IR: 3137 cm$^{-1}$w, 1639 w, 1444 s, 1376 m, 1279 w, 1227 w, 1205 w, 1182 w, 1147 w, 1090 w-m, 982 w, 959 m-w,
902 m-w, 885 w, 868 w, 811 w

Preparation of the Lithium Salts X and Reaction to Give the Chlorodimethylsilyl Derivatives VII 0.1 mol of the diene mixture IX is dissolved in 100 ml of dry hexane and the solution is cooled to 10° C. 69 ml of a 1.6 molar solution of butyllithium is pumped in in the course of half an hour by means of a canula. The initially colorless solution becomes cloudy, and a very flocculant white solid then separates out. After stirring for 3 hours at room temperature, refluxing is continued for 1 hour, the precipitate becoming coarser. It is now filtered off under suction over a No. 3 frit. By washing several times with hexane with complete suspension, it is freed from excess BuLi. It is then dried in a high vacuum to a pulverulent consistency. Yield: 79%

To prepare the chlorodimethylsilyl derivatives VII, the lithium salt is suspended in 50 ml of THF and is pumped into a solution of 35 ml of freshly distilled dichlorodimethylsilane in the same amount of THF. The suspension instantaneously becomes a solution. Occasional cooling with ice keeps the liquid at room temperature. Stirring is continued for 1 hour and the solvent is stripped off completely. The remaining semi-crystalline mass is extracted with 4×30 ml of methylene chloride. The oil remaining after the solvent has been stripped off is distilled in a bulb tube as under 3.

6. Preparation of the Bisdienyldimethylsilyl Derivatives VIII

Equimolar amounts of lithium salt X and chlorodimethylsilyl derivative VII are suspended in toluene and refluxed until chlorodimethylsilyldiene VII is no longer detectable by gas chromatography: 3 h with 20 mmol. The end of the reaction is detected by the fact that the white solid, very finely divided lithium chloride, no longer settles out. The solution is separated off from this by immersion filtration with a capillary which has a very fine-pore filter screwed on upstream, and is evaporated down. Yield: 89%

7. Preparation of the Zirconium Complexes XI

Preparation of the zirconium complex having the bridge ligand VIIIa (n=5)

3.64 g (10 mmol) of the bridge ligand VIIIa are dissolved in 50 ml of ether, and 14 ml of 1.7M BuLi are added at 0° C. This solution is stirred for 1 hour at room temperature, after which the solvent is stripped off completely. The remaining oil is stirred for a further hour. It is then taken up in 40 ml of DME and the solution is cooled to −45° C. This solution, which is cloudy in some cases, is pumped into a solution of 2.32 g of ZrCl$_4$ in 40 ml of DME, which solution is at the same temperature and may contain needles of ZrCl$_4$ which have separated out again. The mixture is allowed to warm up to room temperature in the course of 2 hours, and a clear solution is obtained. This is stirred overnight, and a white precipitate separates out. The solution is now kept at 80° C. for a further 3 hours. The fine white precipitate agglomerates appreciably, and an oil separates out. The supernatant solution is poured off and the oil is dissolved in methylene chloride and filtered off from insoluble LiCl by means of a capillary frit.

The remaining solution is evaporated to saturation, covered with a layer of hexane and stored in a freezer until crystallization occurs. The complex is obtained as a rac/meso mixture (1:1) in the form of a yellow powder. Yield: 40% of theory $^1$H-NMR (100 MHz, CDCl$_3$, 25° C.): 6.08 S 2H, 2.44 S 6H, 1.78, 1.57, 1.3, 0.93 "M" 10H, 0.69 "T" 6H $^{13}$C-NMR (100 MHz, CDCl$_3$, 25° C.) 121.73, 128.4, 136.1, 137.32, 139.27, 32.74, 31.79, 28.82, 26.8, 26.65, 17.88, 13.8

8. Preparation of the Zirconium Complexes XII

Preparation of the zirconium complex from the cyclopentadienes IX (n=5).

Under a nitrogen atmosphere, 466 mg (2 mmol) of freshly sublimed ZrCl$_4$ are dissolved in 30 ml of dimethoxyethane (DME), which has been cooled to −10° C. After stirring for 20 minutes, the zirconium chloride dissolved in, the solution is cooled to −40° C. and a suspension, at the same temperature, of 612 mg (4 mmol) of lithiumcyclopentadiene X in DME is pumped in. The mixture is allowed to warm up to room temperature over a period of 1-2 hours and is stirred overnight. All solids dissolve. Finally, refluxing is carried out for 3 hours, a fine precipitate of lithium chloride forming. The decanted solution is completely evaporated and then digested with 30 ml of methylene chloride. Stirring is carried out for 10 minutes, after which 10 ml of concentrated HCl are added and stirring is continued for a further 20 minutes. The supernatant methylene chloride is separated off in a separating funnel, the aqueous phase is extracted again with methylene chloride and the combined organic phases are dried with sodium sulfate and evaporated to dryness. The remaining crystalline mass is dissolved in a mixture of 14 ml of methylene chloride and 6 ml of benzene and the solution is heated briefly to the boiling point. Fine, slightly lemon yellow needles are precipitated on cooling.

M.p.: 236° C., yield: 63% of theory $^1$H-NMR (100 MHz, CDCl$_3$, 25° C.), 5.94 S 2H, 2.56 "T" 4H, 2.08, 1.92, 1.8, 1.52, 1.21 "M" 6H $^{13}$C-NMR (100 MHz, CDCl$_3$, 25° C.) 133.14 (O), 121.85 (O), 117.86 (+), 32.23 (−), 30.72 (−), 28.73 (−), 15.63 (+)

Metallocenes XI as Polymerization Catalysts

The meanings are as follows:

| | |
|---|---|
| VN = | Viscosity number in cm$^3$/g |
| M$_w$ = | Weight average molecular weight |
| M$_w$/M$_n$ = | Molecular weight dispersity |
| II = | Isotactic index (II = mm + ½ mr) determined by $^{13}$C-NMR spectroscopy |
| n$_{iso}$ = | Length of the isotactic blocks (in propylene units) (n$_{iso}$ = 1 + 2 mm/mr) determined by $^{13}$C-NMR spectroscopy |

} Determined by gel permeation chromatography

Melting points and heats of fusion $\Delta H_{m.p.}$ were determined by DSC (heating/cooling rate 20° C./min).

EXAMPLE 1

A dry 24 dm$^3$ reactor was flushed with nitrogen and filled with 12 dm$^3$ of liquid propylene.

35 cm$^3$ of a solution of methylaluminoxane in toluene (corresponding to 52 mmol of Al, mean degree of oligomerization n=17) were then added and the batch was stirred for 15 minutes at 30° C. At the same time, 5.3 mg (0.011 mmol) of rac-dimethylsilyl(2-Me-4,5,6,7-tetrahydro-1-indenyl)$_2$zirconium dichloride were dissolved in 13.5 cm$^3$ of a solution of methylaluminoxane in toluene (20 mmol of Al) and preactivated by allowing to stand for 15 minutes. The solution was then added to the reactor and the polymerization system was brought to 70° C. by heating (in the course of 5 minutes) and kept at this temperature for 3 hours by cooling. The activity of the metallocene was 50.3 kg of PP per g of metallocene per h.

VN = 37 cm$^3$/g; M$_w$ = 24,300 g/mol; M$_w$/M$_n$ = 2.4; II = 96.0%; n$_{iso}$ = 62; m.p. = 150°° C.; $\Delta H_{m.p.}$ = 104 J/g.

EXAMPLE 2

Example 1 was repeated, except that 19.5 mg (0.04 mmol) of the metallocene were used and the polymerization temperature was 50° C. The activity of the metallocene was 18.8 kg of PP per g of metallocene per h.

VN = 72 cm$^3$/g; M$_w$ = 64,750 g/mol; M$_w$/M$_n$ = 2.1; II = 96.0%; n$_{iso}$ = 64; m.p. = 154° C.; $\Delta H_{m.p.}$ = 109.5 J/g.

EXAMPLE 3

Example 1 was repeated, except that 58.0 mg (0.12 mmol) of the metallocene were used and the polymerization temperature was 30° C. The activity of the metallocene was 9.7 kg of PP per g of metallocene per h.

VN = 152 cm$^3$/g; M$_w$ = 171,000 g/mol; M$_w$/M$_n$ = 2.2; II = 99.9%; n$_{iso}$ > 500; m.p. = 160° C.; $\Delta H_{m.p.}$ = 103 J/g.

EXAMPLE 4

Example 1 was repeated, except that 6.8 mg (0.015 mmol) of ethylene(2-Me-4,5,6,7-tetrahydro-1-indenyl)-$_2$zirconium dichloride were used. The metallocene activity was 72.5 kg of PP per g of metallocene per h.

VN = 35 cm$^3$/g; M$_w$ = 20,750 g/mol; M$_w$/M$_n$ = 1.9; II = 94.5%; n$_{iso}$ = 34; m.p. = 141° C.; $\Delta H_{m.p.}$ = 92.4 J/g.

EXAMPLE 5

Example 4 was repeated, except that 28.1 mg (0.062 mmol) of the metallocene were used and the polymerization temperature was 50° C. The metallocene activity was 28.5 kg of PP per g of metallocene per h.

VN = 51 cm$^3$/g; M$_w$ = 28,200 g/mol; M$_w$/M$_n$ = 2.2 II = 94 8%; n$_{iso}$ = 35; m.p. = 143° C.; $\Delta H_{m.p.}$ = 97.9 J/g.

EXAMPLE 6

Example 4 was repeated, except that 50 mg (0.110 mmol) of the metallocene were used and the polymerization temperature was 30° C. The metallocene activity was 10.9 kg of PP per g of metallocene per h.

VN = 92 cm$^3$/g; M$_w$ = 93,800 g/mol; M$_w$/M$_n$ = 2.2; II = 95.5%; n$_{iso}$ = 48; m.p. = 151° C.; $\Delta H_{m.p.}$ = 99.0 J/g.

We claim:

1. A process for the preparation of a compound of the formula XI

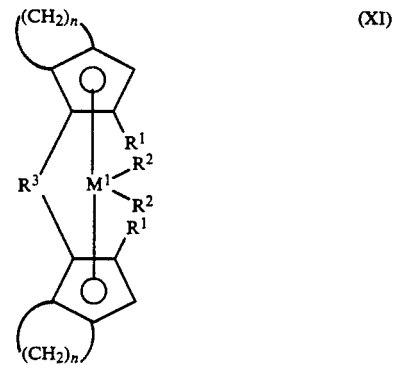

wherein

M$^1$ is a metal from the group comprising titanium, zirconium, hafnium, vanadium, niobium and tantalum, the radicals R$^1$ are identical or different and are hydrogen a C$_1$-C$_{10}$-alkyl group, a C$_6$-C$_{10}$-aryl group, a C$_7$-C$_{15}$-arylalkyl group or a C$_2$-C$_{10}$-alkenyl group, the radicals R$^2$ are identical or different and are a C$_1$-C$_{10}$-alkyl group, a C$_1$-C$_{10}$-alkoxy group, a C$_6$-C$_{10}$-aryl group, a C$_6$-C$_{10}$-aryloxy group, a C$_2$-C$_{10}$-alkenyl group, a C$_7$-C$_{40}$-arylalkyl group, a C$_7$-C$_{40}$-alkylaryl group, a C$_8$-C$_{40}$-arylalkenyl group or a halogen atom, R$^3$ is

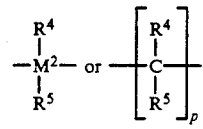

in which

M² is silicon, germanium or tin,

R⁴ and R⁵ are identical or different and are a hydrogen atom, a halogen atom, a $C_1$-$C_{10}$-alkyl group, a $C_6$-$C_{10}$-aryl group, a $C_2$-$C_{10}$-alkenyl group, a $C_7$-$C_{40}$-arylalkyl group, a $C_8$-$C_{40}$-arylalkenyl group or a $C_7$-$C_{40}$-alkylaryl group or R⁴ and R⁵, together with the atom which binds them, form a ring and p is 1, 2 or 3, and n is an integer from 2 to 18, comprising reacting a compound of the formula II

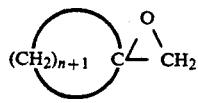 (II)

wherein n is defined above, with an alkali metal or alkaline earth metal salt of a malonic ester, reacting the intermediate formed, without isolation, with a compound R¹-X, in which R¹ has the stated meaning and X is a nucleophilic leaving group, and converting the reaction product by decarboxylation into a lactone of the formula IV

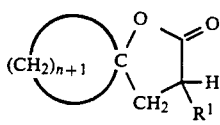 (IV)

wherein n and R¹ are defined above, which is subjected to a rearrangement reaction to give the corresponding enone of formula (V)

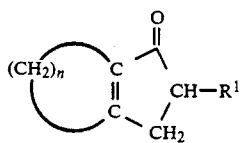 (V)

wherein n and R¹ are defined above and then either step a) reducing by reducing agents or step b) reacting by the "Bamford-Stevens method";

with steps a) or b) followed by reacting with an alkali metal salt, then reacting with a compound M³-R₁ in which M³ is an alkali metal and R₁ is alkyl or hydrogen and then reacting with a compound of the formula M¹X₄ in which X is halogen and M¹ is defined above, to give the compound of the formula XI.

2. The process as claimed in claim 1, wherein, in the formula XI, M¹ is titanium, zirconium or hafnium, the radicals R¹ are identical and are a $C_1$-$C_4$-alkyl group, the radicals R² are identical and are halogen or a $C_1$-$C_4$-alkyl group, M² is silicon, R⁴ and R⁵ are identical or different and are hydrogen or a $C_1$-$C_4$-alkyl group, p is 1 or 2 and n is an integer from 4 to 7.

3. The process as claimed in claim 1, wherein, in the formula XI, M¹ is zirconium, the radicals R¹ are identical and are methyl or ethyl, the radicals R² are identical and are chlorine or methyl, M² is silicon, R⁴ and R⁵ are hydrogen or methyl, p is 2 and n is an integer from 4 to 7.

4. The process as claimed in claim 1, wherein the malonic ester used is a di-($C_1$-$C_4$)-alkyl malonate, and the alkali metal salt used is the corresponding sodium salt.

5. A compound of the formula XI as claimed in claim 1, wherein n is not 4.

6. A compound of the formula XI as claimed in claim 5, wherein M¹ is titanium, zirconium or hafnium, the radicals R¹ are identical and are a $C_1$-$C_4$-alkyl group, the radicals R² are identical and are halogen or a $C_1$-$C_4$-alkyl group, M² is silicon, R⁴ and R⁵ are identical or different and are hydrogen or a $C_1$-$C_4$-alkyl group, p is 1 or 2 and n is an integer from 5 to 7.

7. A compound of the formula XI as claimed in claim 5, wherein M¹ is zirconium, the radicals R¹ are identical and are methyl or ethyl, the radicals R² are identical and are chlorine or methyl, M² is silicon, R⁴ and R⁵ are hydrogen or methyl, p is 2 and n is an integer from 5 to 7.

8. The process as claimed in claim 4, wherein the malonic ester used is diethyl malonate.

9. The process as claimed in claim 1, wherein the malonic ester used is alkyl, aryl or alkenyl ester of a malonic acid.

10. The process as claimed in claim 1, wherein X in the compound R¹-X is a halogen or tosyl.

11. The process as claimed in claim 10, wherein the halogen is bromine or iodine.

12. The process as claimed in claim 1, wherein X in the compound of the formula M¹X₄ is chlorine.

13. The process as claimed in claim 12, wherein the compound M¹X₄ is zirconium terachloride.

14. The process as claimed in claim 1, wherein the Bamford-Stevens method is used.

15. The process as claimed in claim 1, wherein step a) further comprises of reacting with a tosylhydrazine to give a tosylhydrazone (VI)

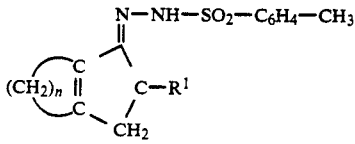 (VI)

wherein n and R¹ are defined in claim 1, which is further reacted by a Bamford-Stevens reaction.

16. The process as claimed in claim 1, wherein step b) further comprises reducing by reducing agents to a diene (IX)

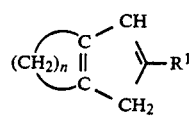 (IX)

wherein n and R¹ are defined in claim 1, which is further reacted with a compound M³-R, in which M³ is an alkali metal and R is alkyl or hydrogen to give the alkali metal salt (X)

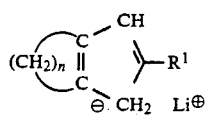 (X)

wherein n and $R^1$ are defined in claim 1, and introduction of the bridge $R^3$ by reaction with a compound $X-R^3-X$ in which X is Cl, Br or tosyl.

17. The process as claimed in claim 15, wherein step b) further comprises of reducing by reducing agents to a diene (IX)

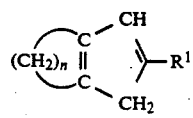 (IX)

wherein n and $R^1$ are defined in claim 15, which is further reacted with a compound $M^3$-R, in which $M^3$ is an alkali metal and R is alkyl or hydrogen to give the alkali metal salt (X)

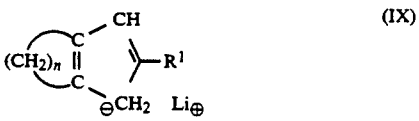 (X)

wherein n and $R^1$ are defined in claim 15, and introduction of the bridge $R^3$ by reaction with a compound $X-R^3-X$ in which X is Cl, Br or tosyl.

* * * * *

UNITED STATES PATENT AND TRADEMARK OFFICE
CERTIFICATE OF CORRECTION

PATENT NO. : 5,268,495
DATED : December 7, 1993
INVENTOR(S) : Riepl et al

It is certified that error appears in the above-indentified patent and that said Letters Patent is hereby corrected as shown below:

In columns 3 and 4 after line 55 and up to column 5, line 33, delete the formulas of Scheme 2 and replace them with the following formula:

Scheme 2

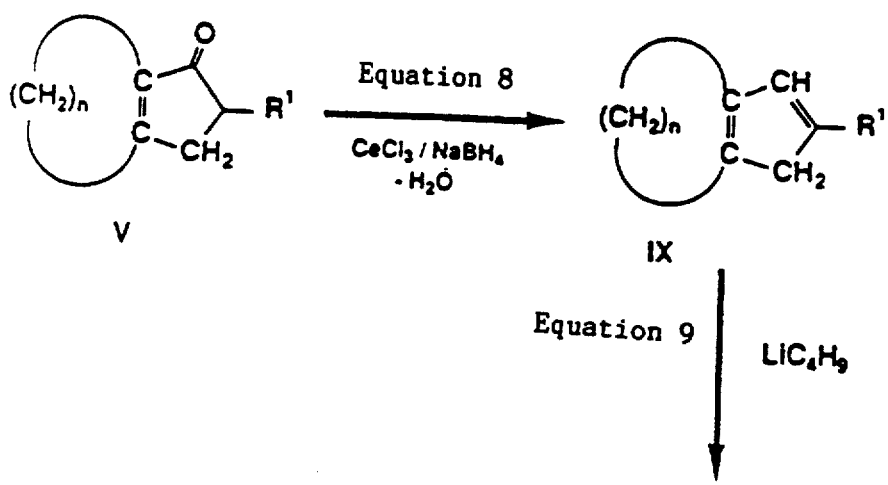

UNITED STATES PATENT AND TRADEMARK OFFICE
CERTIFICATE OF CORRECTION

PATENT NO. : 5,268,495

DATED : December 7, 1993

INVENTOR(S) : Riepl et al

Page 2 of 3

It is certified that error appears in the above-indentified patent and that said Letters Patent is hereby corrected as shown below:

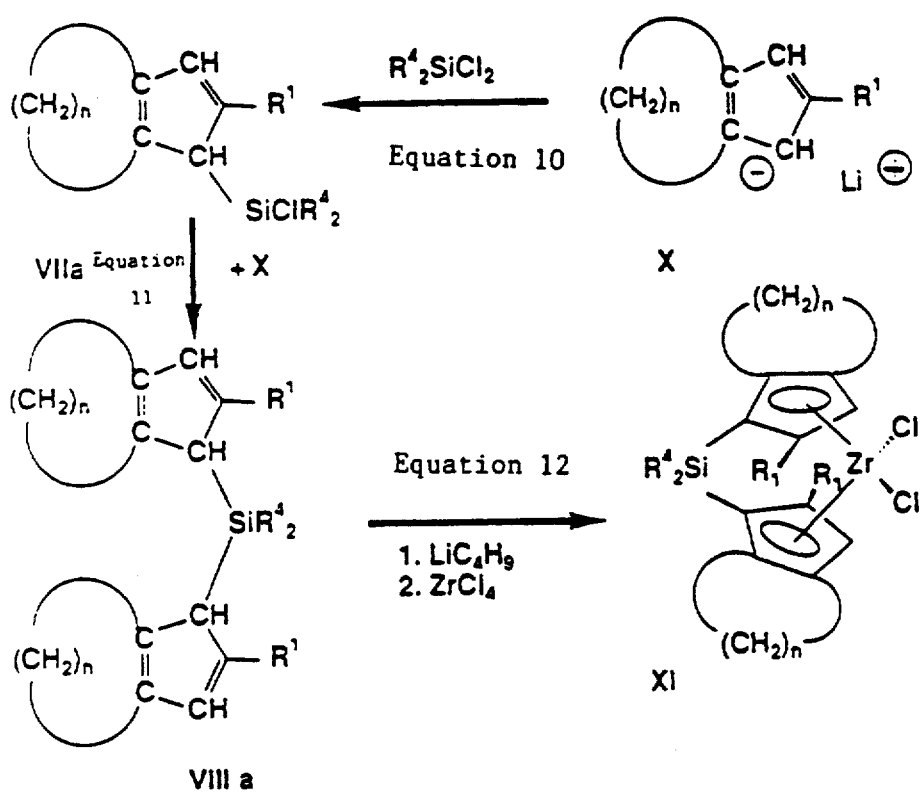

UNITED STATES PATENT AND TRADEMARK OFFICE
CERTIFICATE OF CORRECTION

PATENT NO. : 5,268,495
DATED : December 7, 1993
INVENTOR(S) : Riepl et al

It is certified that error appears in the above-indentified patent and that said Letters Patent is hereby corrected as shown below:

or for the preparation of unbridged metallocenes

2 X + ZrCl$_4$ $\longrightarrow$

Equation 13

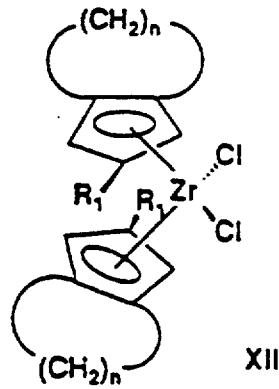

Signed and Sealed this

Fourth Day of October, 1994

Attest:

BRUCE LEHMAN

Attesting Officer

Commissioner of Patents and Trademarks